United States Patent [19]

Lessor et al.

[11] Patent Number: 5,621,115
[45] Date of Patent: Apr. 15, 1997

[54] METHODS FOR PREPARING 5-AROYL-1,2-DIHYDRO-3H-PYRROLO-[1,2-A]PYRROLE-1-CARBOXYLIC ACIDS

[75] Inventors: Ralph A. Lessor, New Providence; Linas V. Kudzma, Annandale; Keith Ramig, Orange, all of N.J.

[73] Assignee: Ohmeda Pharmaceutical Products Division Inc., Liberty Corner, N.J.

[21] Appl. No.: 604,551

[22] Filed: Feb. 21, 1996

[51] Int. Cl.$^6$ ............... C07D 487/04; C07D 207/12; C07D 207/16
[52] U.S. Cl. ............... 548/453; 548/530; 548/543
[58] Field of Search .................. 548/530, 453, 548/543

[56] References Cited

U.S. PATENT DOCUMENTS

| | | | |
|---|---|---|---|
| 4,087,539 | 5/1978 | Muchowski et al. | 424/274 |
| 4,089,969 | 5/1978 | Muchowski et al. | 424/274 |
| 4,097,579 | 6/1978 | Muchowski et al. | 424/274 |
| 4,140,698 | 2/1979 | Van Horn et al. | 260/326.55 M |
| 4,344,943 | 8/1982 | Muchowski | 424/245 |
| 4,347,185 | 8/1982 | Muchowski et al. | 260/326.25 |
| 4,347,186 | 8/1982 | Muchowski et al. | 578/514 |
| 4,347,187 | 8/1982 | Muchowski et al. | 548/516 |
| 4,353,829 | 10/1982 | Thurber et al. | 260/326.25 |
| 4,456,759 | 6/1984 | Muchowski et al. | 548/453 |
| 4,458,081 | 7/1984 | Muchowski et al. | 548/453 |
| 4,496,741 | 1/1985 | Doherty | 514/413 |
| 4,505,927 | 3/1985 | Muchowski et al. | 548/453 |
| 4,835,288 | 5/1989 | Khatri et al. | 548/453 |
| 4,849,526 | 7/1989 | Fleming et al. | 548/453 |
| 4,873,340 | 10/1989 | Muchowski et al. | 548/453 |
| 4,874,871 | 10/1989 | Fleming et al. | 548/453 |
| 4,988,822 | 1/1991 | Muchowski et al. | 548/539 |
| 5,082,950 | 1/1992 | Muchowski et al. | 548/453 |
| 5,082,951 | 1/1992 | Muchowski et al. | 548/539 |

Primary Examiner—David B. Springer
Attorney, Agent, or Firm—R. Hain Swope; Roger M. Rathbun; Salvatore P. Pace

[57] ABSTRACT

This invention pertains to methods for preparing 5-aroyl-1,2-dihydro-3H-pyrrolo-[1,2-a]pyrrole-1-carboxylic acids represented by formula (I):

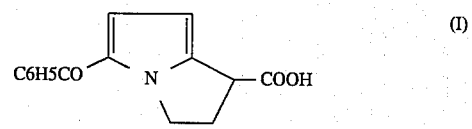

In a first embodiment, the method comprises the sequential steps of cyclizing, via a free radical ring closure reaction, and hydrolyzing a compound represented by formula (IV):

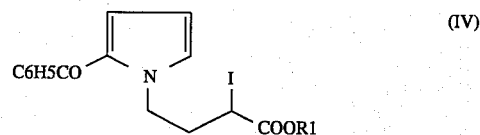

wherein $R_1$ is lower alkyl.

In a second embodiment, the method comprises the sequential steps of hydrolyzing and decarboxylating a compound represented by formula (VIII):

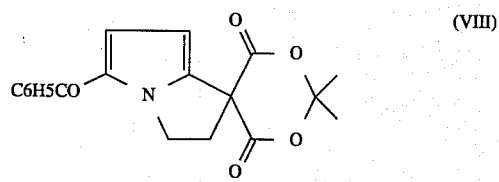

22 Claims, No Drawings

METHODS FOR PREPARING 5-AROYL-1,2-DIHYDRO-3H-PYRROLO-[1,2-A]PYRROLE-1-CARBOXYLIC ACIDS

BACKGROUND OF THE INVENTION

1. Field of the Invention

The present invention relates to methods for preparing 5-aroyl-1,2-dihydro-3H-pyrrolo-[1,2-a]pyrrole-1-carboxylic acids (ketorolac) represented by formula (I):

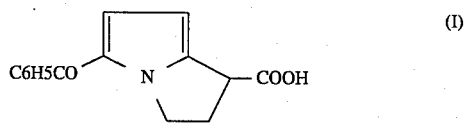

(I)

The present invention also relates to novel intermediates useful preparing the 5-aroyl-1,2-dihydro-3H-pyrrolo-[1,2-a]pyrrole-1-carboxylic acids (I) and to methods for preparing the novel intermediates.

2. Description of the Background

U.S. Pat. Nos. 4,089,969, 4,344,943, and 4,505,927 disclose 5-aroyl-1,2-dihydro-3H-pyrrolo-[1,2-a]pyrrole-1-carboxylic acids. U.S. Pat. No. 4,496,741 discloses a method for preparing 5-aroyl-1,2-dihydro-3H-pyrrolo-[1,2-a]pyrrole-1-carboxylic acids by selective decarboxylation. In all these patents, the methods for preparing these compounds are different from those described herein.

U.S. Pat. No. 4,097,579 discloses 5-aroyl-1,2-dihydro-3H-pyrrolo-[1,2-a]pyrrole-1-carboxylic acids wherein the benzoyl group is replaced with a pyrrolyl group. U.S. Pat. No. 4,087,539 discloses 5-aroyl-1,2-dihydro-3H-pyrrolo-[1,2-a]pyrrole-1-carboxylic acids wherein the benzoyl group is replaced with a furoyl or thienoyl group.

U.S. Pat. No. 4,347,185 discloses a synthesis of 5-benzoyl-7-halo-1,2-dihydro-3H-pyrrolo[1,2-a]pyrrole-1,1-dicarboxylic acid dialkyl diesters by a route different from that described herein, and their subsequent hydrolysis and decarboxylation to 5-benzoyl-7-halo-1,2-dihydro-3H-pyrrolo[1,2-a]pyrrole-1-carboxylic acids.

U.S. Pat. Nos. 4,347,186 and 4,347,187 discloses a synthesis of 5-aroyl-1,2-dihydro-3H-pyrrolo[1,2-a]pyrrole-1,1-dicarboxylic acid dialkyl diesters by a route different from that described herein, and their subsequent hydrolysis and decarboxylation to 5-aroyl-1,2-dihydro-3H-pyrrolo[1,2-a]pyrrole-1-carboxylic acids.

U.S. Pat. No. 4,459,759 discloses 5-benzoyl-7-halo-1,2-dihydro-3H-pyrrolo[1,2-a]pyrrole-1,1-dicarboxylic acid dialkyl diesters and dicarboxylic acids.

U.S. Pat. No. 4,873,340 discloses a synthesis of 5-aroyl-1,2-dihydro-3H-pyrrolo[1,2-a]pyrrole-1,1-dicarboxylic acid dialkyl diesters by a route different from that described herein.

U.S. Pat. No. 4,988,822 discloses intermediates in the synthesis of 5-(substituted aroyl)-1,2-dihydro-3H-pyrrolo[1,2-a]pyrrole-1,1-dicarboxylic acid dialkyl diesters.

U.S. Pat. No. 4,458,081 discloses 5-aroyl-1,2-dihydro-3H-pyrrolo[1,2-a]pyrrole-1,1-dicarboxylic acid dialkyl diesters, monoalkyl monoester, and diacids.

U.S. Pat. No. 5,082,950 discloses the preparation of 5-aroyl-1,2-dihydro-3H-pyrrolo[1,2-a]pyrrole-1,1-dicarboxylic acid dialkyl diesters via the intermolecular free radical coupling of a malonate diester derivative to the 5-position of the 2-aroylpyrrole.

U.S. Pat. No. 5,082,951 discloses the preparation of 5-aroyl-1,2-dihydro-3H-pyrrolo[1,2-a]pyrrole-1,1-dicarboxylic acid dialkyl diesters via the intramolecular free radical coupling of the corresponding malonate diester derivatives to the 5-position of the 2-aroylpyrrole.

U.S. Pat. Nos. 4,835,288, 4,874,871, 4,353,829, 4,140,698, and 4,849,526 discloses methods for preparing intermediates useful for the synthesis of 5-aroyl-1,2-dihydro-3H-pyrrolo-[1,2-a]pyrrole-1-carboxylic acids, the intermediates being different from those described herein.

SUMMARY OF THE INVENTION

This invention pertains to methods for preparing 5-aroyl-1,2-dihydro-3H-pyrrolo-[1,2-a]pyrrole-1-carboxylic acids represented by formula (I):

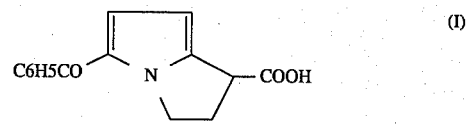

(I)

In a first embodiment, the method for preparing compound (I) comprises the sequential steps of cyclizing, via a free radical ring closure reaction, and hydrolyzing a compound represented by formula (IV):

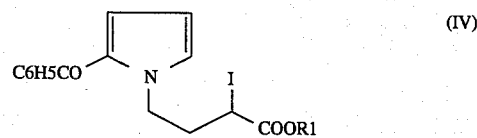

(IV)

wherein $R_1$ is lower alkyl.

In a second embodiment, the method for preparing compound (I) comprises the sequential steps of hydrolyzing and decarboxylating a compound represented by formula (VIII):

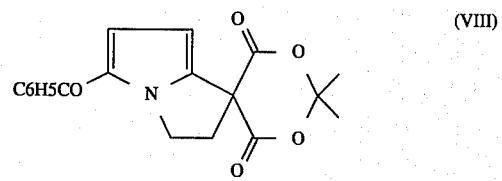

(VIII)

The present invention also relates to novel intermediates (IV) and (VIII) useful for preparing the 5-aroyl-1,2-dihydro-3H-pyrrolo-[1,2-a]pyrrole-1-carboxylic acids (I) and to methods for preparing the novel intermediates.

In one method, compound (IV) is prepared by a process which comprises the sequential steps of treating a compound represented by formula (III):

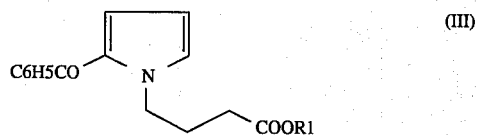

(III)

with a strong, non-nucleophilic base and an electrophilic iodogenous reagent, wherein $R_1$ is lower alkyl.

In another method, compound (IV) is prepared by a process which comprises the sequential steps of hydrolyzing and decarboxylating a compound represented by formula (VIIb):

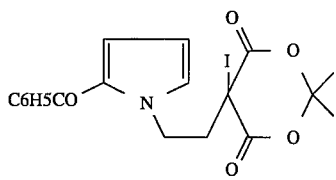 (VIIb)

In still another method, compound (VIII) is prepared by a process which comprises cyclizing, via a free radical ring closure reaction, a compound represented by formula (VII):

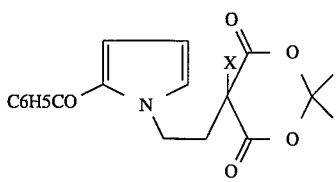 (VII)

wherein X is bromine or iodine. In yet another method, compound (VII) is prepared by a process which comprises treating a compound represented by formula (VI):

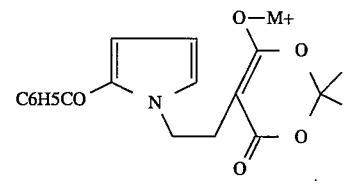 (VI)

with an electrophilic halogenous reagent, wherein M+ is an alkali metal cation.

DETAILED DESCRIPTION OF THE INVENTION

The present invention pertains to methods for preparing 5-aroyl-1,2-dihydro-3H-pyrrolo-[1,2-a]pyrrole-1-carboxylic acids (ketorolac) represented by formula (I):

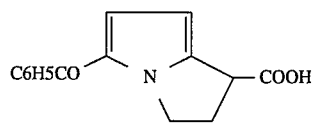 (I)

These carboxylic acids are known to have useful analgesic, antiinflammatory, and antipyretic activities.

In a first embodiment (Route 1), the method comprises the sequential steps of cyclizing, via a free radical ring closure reaction, and hydrolyzing a compound represented by formula (IV):

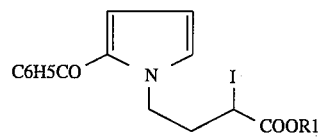 (IV)

wherein $R_1$ is lower alkyl, preferably methyl.

The novel 4-(2-benzoylpyrrol-1-yl)-2-iodobutyric acid esters (IV) are useful intermediates in the preparation of 5-benzoyl-1,2-dihydro-3H-pyrrolo[1,2-a]pyrrole-1-carboxylic acids (I). The iodo compounds (IV) may be prepared by treating the corresponding 4-(2-benzoylpyrrol-1-yl)butyric acid esters (III) with a strong, non-nucleophilic base and an electrophilic iodogenous reagent or, alternatively, by hydrolyzing and decarboxylating intermediate (VIIb). The iodo compounds (IV) are convened to the corresponding 5-benzoyl-1,2-dihydro-3H-pyrrolo[1,2-a]pyrrole-1-carboxylic acids (I) via a free radical ring closure reaction followed by hydrolysis. In a first method, compound (IV) in Route 1 is prepared by the process set out below in Scheme 1.

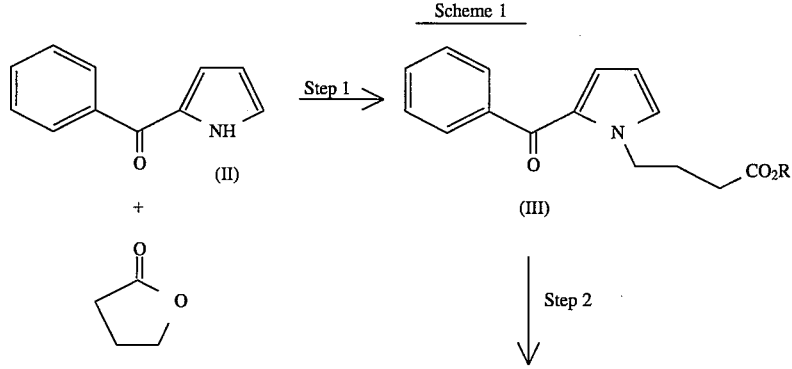

-continued
Scheme 1

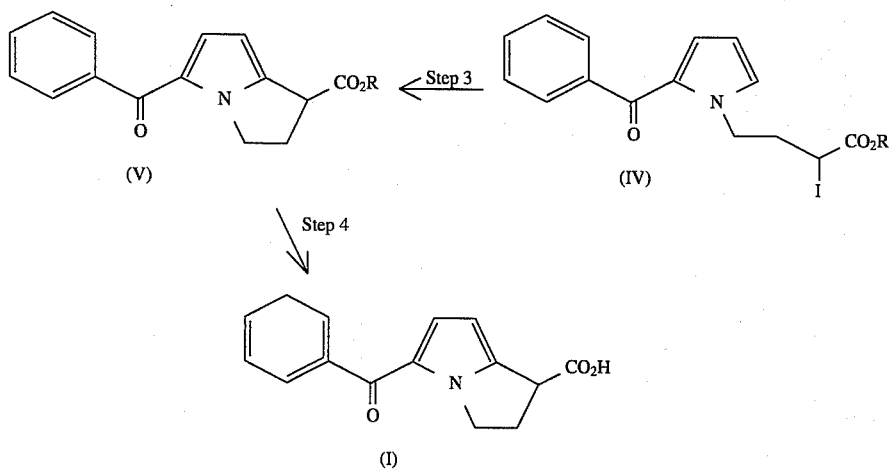

As set out in Scheme 1, 2-benzoylpyrrole (II, prepared according to known procedures, e.g., *J. Org. Chem.* 1977, 42, 4248) is N-alkylated in step 1 with gamma-butyrolactone to provide, after esterification, 4-(2-benzoylpyrrol-1-yl)butyric acid methyl ester (III). 4-(2-Benzoylpyrrol-1-yl)butyric acid methyl ester (III) is then iodinated in step 2 with lithium diisopropylamide and a source of electrophilic iodine, such as iodine, iodine monochloride, or N-iodosuccinimide, to yield 4-(2-benzoylpyrrol-1-yl)-2-iodobutyric acid methyl ester (IV). 4-(2-Benzoylpyrrol-1-yl)-2-iodobutyric acid methyl ester (IV) is then cyclized in step 3 via a free radical ring closure reaction, for example, with hydrogen peroxide and iron (II) sulfate heptahydrate in dimethylsulfoxide, to yield 5-benzoyl-1,2-dihydro-3H-pyrrolo[1,2-a]pyrrole-1-carboxylic acid methyl ester (V). 5-Benzoyl-1,2-dihydro-3H-pyrrolo[1,2-a]pyrrole-1-carboxylic acid methyl ester (V) is then hydrolyzed in step 4 to the corresponding acid (I, ketorolac) by known procedures, e.g., U.S. Pat. No. 4,089,969.

Preparation of 4-(2-Benzoylpyrrol-1-yl)butyric Acid (III), (Step 1, Scheme 1).

4-(2-Benzoylpyrrol-1-yl)butyric acid (III, R=H) is prepared by alkylation of an alkali metal salt of the known 2-benzoylpyrrole with gamma-butyrolactone (for an example of a similar alkylation, see *J. Org. Chem.* 1993, 58, 516). The formation of the alkali metal salt of 2-benzoylpyrrole is carried out by reaction of the pyrrole with an alkali metal hydride, optionally in the presence of a polar aprotic organic solvent. Among the solvents which may be advantageously employed are ethereal solvents, such as tetrahydrofuran, diethyl ether, dioxane, glyme, diglyme, and the like. Formation of the alkali metal salt of the pyrrole is carried out under an inert atmosphere, such as nitrogen, argon, and the like, by addition of the 2-benzoylpyrrole, preferably as a solution in a polar aprotic organic solvent, to the alkali metal hydride, which may optionally be suspended in a polar aprotic organic solvent. The alkali metal hydride is preferably present in slight excess relative to the 2-benzoylpyrrole, more preferably in an amount from about 1.01 to abut 1.1 molar equivalents relative to the 2-benzoylpyrrole. The addition is preferably carried out over as brief a period as possible, making allowance for the evolution of hydrogen gas and heat which ensues. External cooling of the reaction vessel may be optionally and advantageously employed to moderate the rate of reaction. The formation of the alkali metal salt of the 2-benzoylpyrrole is allowed to proceed to completion over a period of time ranging from about 5 minutes to about 4 hours, preferably from about 30 to about 60 minutes. The crude alkali metal salt of the 2-benzoylpyrrole is then rendered substantially free of volatile organic solvent, if such solvent was employed, by evaporation of said solvent under reduced pressure.

Reaction of the alkali metal salt of 2-benzoylpyrrole with gamma-butyrolactone carried out employing the lactone in slight excess, preferably from about 1.05 to about 1.2 molar equivalents relative to the amount of 2-benzoylpyrrole employed in the formation of the alkali metal salt. The reaction may be carried out in the presence of high-boiling, polar aprotic organic solvent, but is preferably carried out in the absence of such solvent. The reaction is carried out with protection from moisture, optionally under an inert atmosphere such as nitrogen, argon or the like, by combining the alkali metal salt and the lactone and heating the resulting mixture at a temperature from about 100° C. to about 160° C. preferably from about 130° C. to about 140° C., for a period from about three to about eight hours, preferably about four to about six hours, and then allowing the reaction mixture to cool to ambient temperature. 4-(2-Benzoylpyrrol-1-yl)butyric acid (III, R=H) is isolated from the resulting glassy solid by conventional means.

In a preferred embodiment, the glassy solid is dissolved in water or in a dilute aqueous solution of an alkali metal hydroxide or carbonate. This solution is then washed with a water-immiscible polar organic solvent, such as diethyl ether, ethyl acetate, or a halogenated hydrocarbon solvent such as dichloromethane or chloroform. The aqueous solution is then acidified with a mineral acid and extracted with a water-immiscible polar organic solvent, such as diethyl ether, ethyl acetate, or the like, or a halogenated hydrocarbon solvent such as dichloromethane or chloroform. The organic extract is then dried and evaporated under reduced pressure to afford 4-(2-benzoylpyrrol-1-yl) butyric acid (III, R=H).

Preparation of 4-(2-Benzoylpyrrol-1-yl)butyric Acid Esters (III, R=Lower Alkyl), (Step 1, Scheme 1).

Lower alkyl esters of 4-(2-benzoylpyrrol-1-yl)butyric acid may be prepared by means known to those skilled in the art, such as by reacting the acid with a lower alkanol in the presence of an acid catalyst. A preferred ester, the methyl ester, may be prepared by reacting the acid with an excess of methanol, which also serves as solvent, in the presence of an acid catalyst. Suitable acid catalysts include mineral acids and strong organic acids such as alkanesulfonic or arylsulfonic acids. A preferred acid catalyst is sulfuric acid. The reaction is carried out by dissolving the 4-(2-benzoylpyrrol-1-yl)butyric acid in an excess of the desired lower alkanol, adding the desired acid catalyst, and stirring the mixture until the reaction is substantially complete. The reaction is conducted at a temperature between ambient temperature and the boiling point of the lower alkanol, preferably at the boiling point, for a period or time ranging from about 30 minutes to about 24 hours, preferably from about one to about three hours. Isolation of the product may then be carried out by conventional means, such as by extraction, chromatography, and the like.

Preparation of 4-(2-Benzoylpyrrol-1-yl)-2-iodobutyric Acid Esters (IV) by Direct Iodination, (Step 2, Scheme 1).

4-(2-Benzoylpyrrol-1-yl)-2-iodobutyric acid esters (IV) may be prepared from 4-(2-benzoylpyrrol-1-yl)butyric acid esters by reaction of the enolate anion or trialkylsilyl enol ether derived therefrom by reaction with a source of electrophilic iodine. Formation of the enolate or trialkylsilyl enol ether and subsequent reaction with a source of electrophilic iodine may be carried out in ethereal solvents, such as tetrahydrofuran, diethyl ether, dioxane, glyme, diglyme, and the like, or in a mixture of such solvent with one or more hydrocarbon solvents, such as hexane, benzene and the like. In one embodiment, formation of the enolate anion of a 4-(2-benzoylpyrrol-1-yl)butyric acid ester may be carried out by reaction of the ester with a strong, non-nucleophilic organic base, preferably an alkali metal amide base such as lithium diisopropylamide. Formation of the enolate may be carried out at a temperature between about −80° C. and about −30° C., preferably at about −78° C., and for a period of time from about one minute to about 90 minutes. The strong organic base is added as a solution, in an amount of from about 0.9 to about 1.2 molar equivalents relative to the ester, preferably from about 1.05 to about 1.1 molar equivalents. The addition of the base is preferably made over as short a period of time as possible while maintaining the temperature of the reaction mixture within the preferred range.

Subsequent to formation of the enolate anion, a source of electrophilic iodine is added to the reaction mixture. Suitable sources of electrophilic iodine are elemental iodine, iodine monochloride, N-iodosuccinimide, carbon tetraiodide, and the like, with elemental iodine or iodine monochloride being preferred. The source of electrophilic iodine may be added to the mixture in pure form, or as a solution in a suitable solvent, as will be obvious to one skilled in the art. Reaction of the enolate anion with the source of electrophilic iodine is carried out at a temperature between about −80° C. and about 25° C. In a preferred embodiment, the reaction is carried out initially at a temperature from about −80° C. to about −60° C. for a period from about 5 minutes to about one hour, then the reaction mixture is allowed to warm slowly to ambient temperature. The product of the reaction, a 4-(2-benzoylpyrrol-1-yl)-2-iodobutyric acid ester (IV), may then be isolated by means known to those skilled in the art, such as by extraction, chromatography, and the like.

In another embodiment, the enolate anion is trapped in situ as a trialkylsilyl enol ether prior to reaction with the source of electrophilic iodine in order to suppress undesirable self-condensation of the enolate. In this embodiment, formation of the enolate anion is carried out in the presence of a trialkylsilyl chloride, present in the reaction medium in an amount from about one to five molar equivalents relative to the ester. Formation of the enolate anion and trapping of the anion as the silyl enol ether is carried out essentially as previously described by addition of a strong, non-nucleophilic organic base, preferably an alkali metal amide, to a solution of the ester and the trialkylsilyl chloride in a suitable solvent, as defined previously for formation of the enolate. Subsequent to formation of the trialkylsilyl enol ether, a source of electrophilic iodine, as defined previously for the iodination of the enolate anion, is added to the reaction medium. Reaction of the trialkylsilyl enol ether with the source of electrophilic iodine is carried out under substantially the same conditions as described previously for the iodination of the enolate anion, except that longer reaction times may be employed when a less reactive source of electrophilic iodine is employed, as will be obvious to those skilled in the art. Isolation of the iodoester product may be carried out as previously described by means known to those skilled in the art.

Cyclization of of 4-(2-Benzoylpyrrol-1-yl)-2-iodobutyric Acid Esters (IV) to 5-Benzoyl-1,2-dihydro-3H-pyrrolo[1,2-a]pyrrole-1-carboxylic Acid Esters (V), (Step 3, Schemes 1 and 2).

Ring closure of the 4-(2-Benzoylpyrrol-1-yl)-2-iodobutyric acid esters (IV) is carried out by treating the esters with a source of alkyl radicals in a suitable solvent. The choice of solvent depends on the chosen source of alkyl radicals. A preferred alkyl radical, the methyl radical, may be generated by reaction of ferrous sulfate with hydrogen peroxide and dimethylsulfoxide. In this case, the preferred solvent is dimethylsulfoxide or a mixture of dimethylsulfoxide and water. Mixtures of dimethylsulfoxide with other polar solvents may also be employed, with the stipulation that the polar solvent must be unreactive toward the reactive components of the radical-forming system and toward the radical itself. In an alternative preferred embodiment, the alkyl radicals may be generated from a trialkylborane and oxygen in an aprotic solvent.

To a solution of the 4-(2-benzoylpyrrol-1-yl)-2-iodobutyric acid ester (IV), in a suitable solvent, is added a source of alkyl radicals. In a preferred embodiment, this step comprises addition of an aqueous solution of hydrogen peroxide to a solution of the halogenated starting material and ferrous sulfate in dimethylsulfoxide or a mixture of dimethylsulfoxide and a suitable cosolvent, as described above. The ferrous sulfate may be present in an amount from about 0.01 to about 1 mole equivalent relative to the halo compound, preferably from about 0.05 to about 0.25 mole equivalent. The aqueous peroxide solution may contain from about 10% to about 50% by weight of hydrogen peroxide, preferably about 30%. The aqueous peroxide solution is added slowly, in an amount from about 5 to about 20 mole equivalents relative to the iodoester, preferably in an amount from about 6 to about 12 mole equivalents. The addition may be carried out at a temperature in the range from about 20° C. to about 60° C., preferably in the range from about 20° C. to about 30° C. The addition may be made with the application of an external cooling bath to maintain the internal reaction temperature within the preferred range.

In a second preferred embodiment, the source of alkyl radicals is a combination of a trialkylborane and oxygen. In this embodiment, a solution of the iodoester in a suitable solvent is treated with a trialkylborane in the presence of atmospheric oxygen. Suitable solvents are aprotic organic solvents, and a preferred solvent is dimethylsulfoxide. The trialkylborane is added, either in pure form or as a solution in a polar aprotic organic solvent, such as tetrahydrofuran, to the solution of the iodoester in portions over a period from about 1 to about 24 hours, and is taken in excess, preferably from about 2 to about 5 molar equivalents relative to the iodoester. Additions of the trialkylborane, in portions of about 0.5 to about 1 molar equivalent relative to the iodoester, are made periodically (typically every 1–2 hours) until reaction is substantially complete, as judged by thin layer chromatography or other conventional means. The reaction is conducted at a temperature from about 20° C. to about 30° C. in the presence of atmospheric oxygen, which is provided by leaving the reaction vessel open to ambient air, or by passing a slow stream of air over or through the reaction medium.

In either of the embodiments described, the reaction mixture is allowed to stir until the reaction is substantially complete. The mixture is poured into water and extracted with a polar aprotic solvent. The combined organic extracts are washed with water, dried, and concentrated under reduced pressure to yield a compound of formula (V), which may be isolated by conventional means.

In a second method, compound (IV) in Route 1 is prepared by the process set out below in Scheme 2.

5-yl)ethyl]-2-Coenzoyl)pyrrole (VI), according to known procedures, e.g., U.S. Pat. No. 4,347,187. The alkali metal salt of 1-[2[(4,6-dioxo-2,2-dimethyl-1,3-dioxolan-5-yl) ethyl]-2-(benzoyl)pyrrole (VI) is then treated in step 2 with a source of electrophilic iodine, such as iodine, iodine monochloride, N-iodosuccinimide, or a complex between iodine and morpholine, to form the alpha-iodo intermediate (VIIb), which is not isolated, but is converted directly to 4-(2-benzoylpyrrol-1-yl)-2-iodobutyric acid ester (IV) by treatment with an alkali metal lower alkoxide. Alternatively, the sodium salt (VI) may be treated with a lower alkyl hypoiodite (generated in situ by reaction of iodine monochloride with an alkali lower alkoxide or by other means known to those skilled in the art) to provide the iodoester (IV) directly. 4-(2-Benzoylpyrrol-1-yl)-2-iodobutyric acid methyl ester (IV) is then cyclized in step 3 via a free radical ring closure reaction, as set out in Scheme 1, with, for example, hydrogen peroxide and iron (II) sulfate heptahydrate in dimethylsulfoxide to yield 5-benzoyl-1,2-

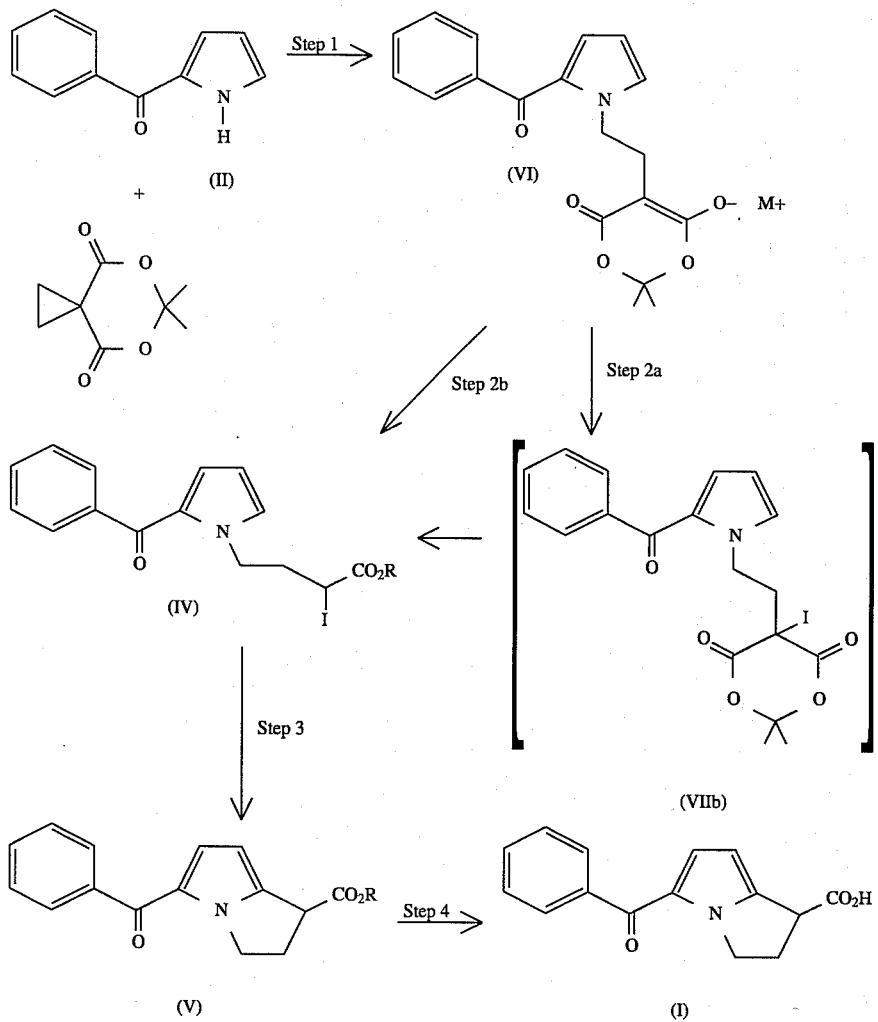

Scheme 2

As set out in Scheme 2, 2-benzoylpyrrole (II, prepared according to known procedures, e.g., *J. Org. Chem.* 1977, 42, 4248) is N-alkylated in step 1 with spiro[2,5]-5,7-dioxa-6,6-dimethyloctane-4,8-dione to form the alkali metal salt of the cyclic diester, 1-[2-(4,6-dioxo-2,2-dimethyl-1,3-dioxan- dihydro-3H-pyrrolo[1,2a]pyrrole-1-carboxylic acid methyl ester (V). 5-Benzoyl-1,2-dihydro-3H-pyrrolo[1,2-a]pyrrole-1-carboxylic acid methyl ester (V) is then hydrolyzed in step 4 to the corresponding acid (I, ketorolac) by known procedures, e.g., U.S. Pat. No. 4,089,969.

Preparation of 4-(2-Benzoylpyrrol-1-yl)-2-iodobutyric Acid Esters (IV) by Solvolysis and Decarboxylation of 1-[2-(5-Iodo-4,6-dioxo-2,2-dimethyl-1,3-dioxan-5-yl)ethyl]-2-(benzoyl)pyrrole, (Step 2a, Scheme 2).

Compounds of Formula VI are prepared according to known procedures (see, e.g., U.S. Pat. No. 4,347,187). Iodination of compounds of Formula VI, wherein M+ is an alkali metal cation, such as sodium, potassium, lithium, and the like, is carried out by treatment with a source of electrophilic iodine in the presence of a polar aprotic organic solvent. Suitable solvents include ethereal solvents such as diethyl ether, tetrahydrofuran, 1,4-dioxane, ethylene glycol dimethyl ether, and the like; and halogenated hydrocarbon solvents such as dichloromethane, 1,2-dichloroethane and the like. The source of electrophilic iodine may be a dihalogen, such as iodine or iodine monochloride, or N-iodosuccinimide. A preferred source of electrophilic iodine is iodine monochloride. A solution of the source of electrophilic iodine is added slowly to a solution or suspension of the alkali metal salt substrate over a period from about 5 minutes to about 5 hours, preferably from about 5 to 30 minutes, at a temperature between about −78° C. and about 25° C. The preferred temperature depends on the reactivity of the iodinating agent, as will be apparent to one skilled in the art: for example, for iodine monochloride, the preferred temperature is between about −78° C. and about 0° C.; for N-iodosuccinimide, the preferred temperature is between about 0° C. and about 25° C.

The product, a compound of formula VII (X=I), is then treated, in situ, with an alkali metal lower alkoxide. A preferred alkoxide is sodium methoxide. The alkali metal lower alkoxide is added as a solution in a suitable solvent, preferably the alcohol corresponding to the alkoxide, and is present in an amount from about one to about two molar equivalents relative to the compound of formula VII, preferably in an amount from about 1.1 to about 1.3 molar equivalents. The additions of the alkoxide is carried out at a temperature between about −78° C. and about 0° C., over a period of about one minute to about one hour, preferably from about one to about five minutes. The reaction is then allowed to proceed for a period of about 3 to about 18 hours, at a temperature between about −78° C. and about 25° C. In a preferred embodiment, the reaction mixture is maintained at a temperature from about −78° C. to about 0° C. for a period of about 1 to about 3 hours, and is then allowed to warm to ambient temperature and stirred for an additional 10 to 15 hours. The product, a compound of formula IV, is isolated by conventional means. In a preferred embodiment, the product is isolated by pouring the reaction mixture into an excess of an aqueous solution of a mild reducing agent, such as sodium sulfite, extracting the product into a polar aprotic organic solvent such as diethyl ether or ethyl acetate, drying of the organic product solution, and removal of solvent.

Preparation of 4-(2-Benzoylpyrrol-1-yl)-2-iodobutyric Acid Esters (IV) by Reaction of the Alkali Metal Salt of 1-[2-(4,6-dioxo-2,2-dimethyl-1,3-dioxan-5-yl)ethyl]-2-(benzoyl)pyrrole with a Lower Alkyl Hypoiodite, (Step 2b, Scheme 2).

4-(2-Benzoylpyrrol-1-yl)-2-iodobutyric acid esters (IV) may also be prepared by direct reaction of an alkali metal salt of 1-[2-(4,6-dioxo-2,2-dimethyl-1,3-dioxan-5-yl)ethyl]-2-(benzoyl)pyrrole, under basic conditions, with a lower alkyl hypoiodite or its equivalent, which may be generated in situ by reaction of an alkali metal lower alkoxide with a source of electrophilic iodine, or by other means known to those skilled in the art. The reaction may be carried out in a solvent consisting of the alcohol corresponding to the selected hypoiodite, or in a mixture of this alcohol and a suitable polar aprotic organic solvent. Suitable solvents for this purpose include ethereal solvents such as tetrahydrofuran, diethyl ether, dioxane, glyme, diglyme and the like, and halogenated organic solvents which are unreactive under the conditions of the reaction, such as dichloromethane and 1,2-dichloroethane a preferred reaction solvent is a mixture of tetrahydrofuran and the alcohol corresponding to the selected hypoiodite.

In one embodiment, a solution of an alkali metal lower alkoxide in a suitable solvent, as defined above, is treated with a source of electrophilic iodine. A preferred source of electrophilic iodine is iodine monochoride, and a preferred alkoxide is sodium methoxide. The alkali metal lower alkoxide is taken in slight excess to the amount of the source of electrtophilic iodine, preferably from about 1.05 to about 1.2 molar equivalents. The source of electrophilic iodine, either neat or as a solution in, for example, dichloromethane, is added to a solution of the alkoxide, over a period from about one to about five minutes as required to maintain the temperature of the reaction mixture in the desired range. This reaction is carried out at a temperature between about −78° C. and about 0° C., preferably between about −30° C. and about −10° C. Subsequent to the addition of the source of electrophilic iodine, the reaction mixture is stirred for about two minutes, then the alkali metal salt of 1-[2-(4,6-dioxo-2,2-dimethyl-1,3-dioxan-5yl)ethyl]-2-(benzoyl)pyrrole is added in portions as a solid. The reaction mixture is stirred at a temperature between about −78° C. and about 0° C., preferably between about −30° C. and about −10° C., for a period of about thirty minutes to about three hours, then allowed to warm to ambient temperature and stirred for an additional 3 to 24 hours. The product, a compound of formula IV, may be isolated by conventional means. In a preferred embodiment, the product is isolated by pouring the reaction mixture into an excess of an aqueous solution of a mild reducing agent, such as sodium sulfite, extracting the product into a polar aprotic organic solvent such as diethyl ether or ethyl acetate, drying of the organic product solution, and removal of solvent.

Other methods of generating the selected lower alkyl hypoiodite or its equivalent, which are known to those skilled in the art, may also be employed, with the stipulation that the method chosen must be compatible with the presence of the alkoxide corresponding to the selected alkyl hypoiodite.

The present invention is also directed to a compound represented by formula (IV):

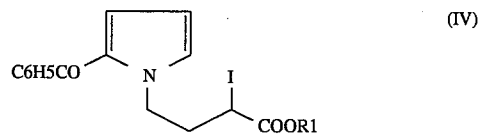

wherein $R_1$ is defined as set out above, and to methods for preparing compound (IV). In one method, compound (IV) is prepared by a process which comprises the sequential steps of treating compound (III) with a strong, non-nucleophilic base and an electrophilic iodogenous reagent. In another method, compound (IV) is prepared by a process which comprises the sequential steps of hydrolyzing and decarboxylating compound (VIIb).

In a second embodiment (Route 2), the present invention is directed at a method for preparing a compound represented by formula (I):

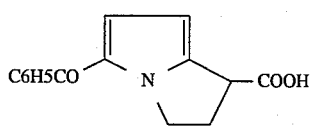

which comprises hydrolyzing and decarboxylating a compound represented by formula (VIII):

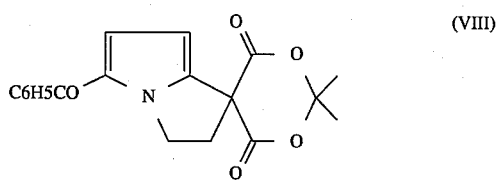

The novel 5-benzoyl-1,2-dihydro-3H-pyrrolo[1,2-a]pyrrole-1-spiro-5'-(2',2'-dimethyl-4',6'-dioxo)-1',3'-dioxolanes (VIII) are useful intermediates in the preparation of 5-benzoyl-1,2-dihydro-3H-pyrrolo[1,2-a]pyrrole-1-carboxylic acids (I). The spirocyclic compounds (VIII) are prepared by free-radical ring-closure of the corresponding 1-[2-(5-bromo-4,6-dioxo-2,2-dimethyl-1,3-dioxan-5-yl)ethyl]-2-(benzoyl)pyrroles or their (5-iodo) analogs (VII). The spirocyclic intermediates (VIII) are convened to the corresponding 5-benzoyl-1,2-dihydro-3H-pyrrolo[1,2-a]pyrrole-1-carboxylic acids (I) by hydrolysis and decarboxylation under mild conditions. The 1-[2-(5-bromo-4,6-dioxo-2,2-dimethyl-1,3-dioxan-5-yl)ethyl]-2-(benzoyl)pyrroles and their (5-iodo) analogs (VII) are also novel and useful intermediates in the synthesis of the spirocyclic compounds (VIII) and in synthesis of the 5-benzoyl-1,2-dihydro-3H-pyrrolo[1,2-a]pyrrole-1-carboxylic acids (I). The method of Route 2 is set out below in Scheme 3.

Scheme 3

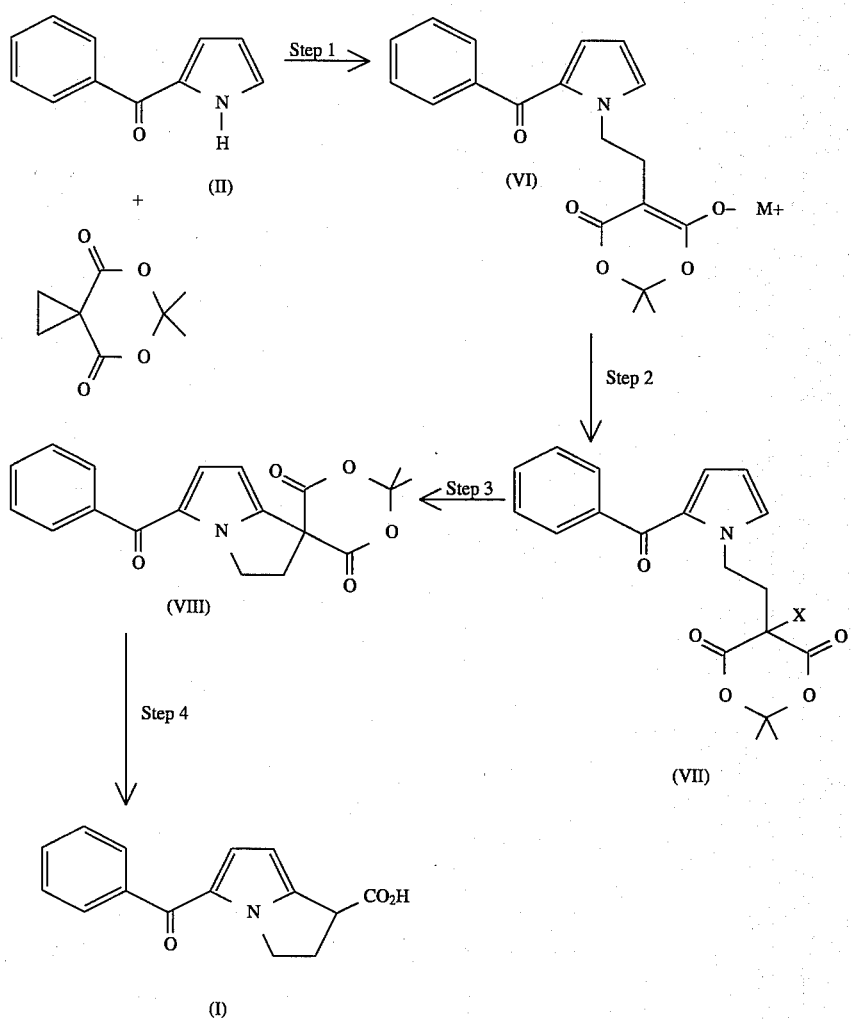

As set out in Scheme 3, 2-benzoylpyrrole (II, prepared according to known procedures, e.g., *J. Org. Chem.* 1977, 42, 4248) is N-alkylated in step 1 with spiro[2,5]-5,7-dioxa-6,6-dimethyloctane-4,8-dione to form the cyclic diester, 1-[2-(4,6-dioxo-2,2-dimethyl-1,3-dioxan-5-yl)ethyl]-2-(benzoyl)pyrrole (VI), according to known procedures, e.g., U.S. Pat. No. 4,347,187.

Preparation of 1-[2-(5-Halo-4,6-dioxo-2,2-dimethyl-1,3-dioxan-5-yl)ethyl]-2-(benzoyl)pyrrole (VII), (Step 2, Scheme 3).

The alkali metal salt of 1-[2[(4,6-dioxo-2,2-dimethyl-1,3-dioxolan-5-yl)ethyl]-2-(benzoyl)pyrrole (VI) is brominated or iodinated in step 2 at the doubly activated alpha-position with a source of electrophilic bromine or iodine to form 1-[2-(5-halo-4,6-dioxo-2,2-dimethyl-1,3-dioxolan-5-yl)ethyl]-2(benzoyl)pyrrol (VII). Alternatively, compound (VII) may be prepared from the neutral form of compound VI, obtained by treatment of VI with mineral acid and extraction into an organic solvent, by treatment with a source of electrophilic bromine or iodine which does not produce a strong acid upon reaction, such as N-bromosuccinimide, or the like.

Halogenation of compounds (VI), wherein M+ is an alkali metal cation, such as sodium, potassium, lithium, and the like, is carried out by treatment with a source of electrophilic halogen in the presence of a polar aprotic organic solvent. Suitable solvents include ethereal solvents such as diethyl ether, tetrahydrofuran, 1,4-dioxane, ethylene glycol dimethyl ether, and the like, and halogenated hydrocarbon solvents including dichloromethane, chloroform, 1,2-dichloroethane, and the like. The source of electrophilic halogen may be a dihalogen, such as bromine, iodine, or iodine monochloride, or may be an N-halogenated compound, such as N-bromo- or N-iodo-succinimide, N-bromo- or N-iodo-acetamide, or the like. In the case of the preparation of the 5-bromo compounds, the source of electrophilic halogen may be the perbromide salt of a suitable amine, preferably pyridinium bromide perbromide or pyrrolidone hydrotribromide. A solution of the source of electrophilic halogen may be added slowly to a solution or suspension of the alkali metal salt substrate over a period from about 5 minutes to about 5 hours, preferably from about 5 to about 30 minutes, at a temperature between about 78° C. and about 25° C. The preferred temperature depends on the reactivity of the halogenating agent. For example, for bromine, the preferred temperature is between about −78° C. and about 0° C; for pyridinium bromide perbromide, the preferred temperature is between about 0° C. and about 25° C. The product, compound (VII), may be isolated by conventional means.

Preparation of 5-Benzoyl-1,2-dihydro-3H-pyrrolo[1,2-a]pyrrole-1-spiro-5'-(2',2'-dimethyl-4',6'-dioxo)-1',3'-dioxolane (VIII), Step 3, Scheme 3).

1-[2-(5-Halo-4,6-dioxo-2,2-dimethyl-1,3-dioxan-5-yl)ethyl]-2-(benzoyl)pyrrole (VII) is cyclized to 5-benzoyl-1,2-dihydro-3H-pyrrolo[1,2-a]pyrrole-1-spiro-5'-(2',2'-dimethyl-4',6'-dioxo)-1',3'-dioxolane (VIII) through a free radical ring closure reaction, carried out by treating compounds (VII) with a source of alkyl radicals in a suitable solvent. The choice of solvent depends on the chosen source of alkyl radicals. A preferred alkyl radical, the methyl radical, may be generated by reaction of ferrous sulfate with hydrogen peroxide and dimethylsulfoxide. In this case, the preferred solvent is dimethylsulfoxide or a mixture of dimethylsulfoxide and water. Mixtures of dimethylsulfoxide with other polar solvents may also be employed, with the stipulation that the polar solvent must be unreactive toward the reactive components of the radical-forming system and toward the radical itself.

The source of alkyl radicals is added to a solution of 1-[2-(5-halo-4,6-dioxo-2,2-dimethyl-1,3-dioxan-5-yl)ethyl]-2-(benzoyl)pyrrole (VII) in a suitable solvent. In a preferred embodiment, this step comprises addition of an aqueous solution of hydrogen peroxide to a solution of the halogenated starting material and ferrous sulfate in dimethylsulfoxide or a mixture of dimethylsulfoxide and a suitable cosolvent, as described above. The ferrous sulfate may be present in an amount from about 0.01 to about 1 mole equivalent relative to the halo compound, preferably from about 0.05 to about 0.25 mole equivalent. An alkali metal bicarbonate may be optionally and advantageously added to the reaction to neutralize acid produced during the course of the reaction. The aqueous peroxide solution may be added slowly, in an amount from about 5 to about 20 mole equivalents relative to the halogenated starting material, preferably in an amount from about 8 to about 12 mole equivalents. Addition may be carried out at temperatures in the range from about 25° C. to about 100° C., preferably from about 35° C. to about 75° C. Addition may be made with the application of an external cooling bath to maintain the internal reaction temperature within the preferred range.

The reaction mixture is stirred until the reaction is complete. The reaction mixture is then diluted with a polar aprotic solvent, such as methylene chloride, ethyl acetate, or the like, in an amount sufficient to dissolve substantially all of the solids which may form during the reaction. The mixture is poured into water and extracted with a polar aprotic solvent. The combined organic extracts are washed with water, dried, and concentrated under reduced pressure to yield compound (VIII), which may be isolated by conventional means.

Decarboxylation of 5-Benzoyl-1,2-dihydro-3H-pyrrolo[1,2-a]pyrrole-1-spiro-5'-(2',2'-dimethyl-4',6'-dioxo)-1',3'-dioxolane (VIII) to form Ketorolac (I), (Step 4, Scheme 3).

5-Benzoyl-1,2-dihydro-3H-pyrrolo[1,2-a]pyrrole-1-spiro-5'-(2',2'-dimethyl-4',6'-dioxo)-1',3'-dioxolane (VIII) is then hydrolyzed and decarboxylated in step 4 by treatment with aqueous acid to yield ketorolac (I). Hydrolysis and decarboxylation may be carried out in mixtures of water and a mineral acid or in mixtures of water and an organic acid, optionally in the presence of an additional water-miscible organic solvent. Suitable mineral acids are hydrochloric acid, hydrobromic acid, sulfuric acid, phosphoric acid, and the like. Suitable organic acids are alkanesulfonic or arylsulfonic acids, and strong carboxylic acids, such as trichloroacetic acid and trifluoroacetic acid. Suitable water-miscible organic solvents which may optionally and advantageously be employed to increase the solubility of the reactants are tetrahydrofuran, 1,4dioxane, glyme, diglyme, dimethylformamide, dimethylsulfoxide, and the like. The reaction may be carried out under an inert atmosphere, e.g., nitrogen, argon and the like. The reaction times and temperatures are not critical, and depend, as will be apparent to those skilled in the art, upon the reactants and the other ingredients of the reaction mixture. Thus, the reaction time can be from about one minute to about four hours, with about one minute to about 30 minutes being preferred, and the reaction temperature can be from about 0° C. to about 100° C. In a preferred embodiment, the hydrolysis and decarboxylation is carried out in a mixture of trifluoroacetic acid and water, in which the trifluoroacetic acid content may range from about 1% to about 80% by volume. In this embodiment, the reaction is carried out in a temperature range from about 25° C. to about 100° C.

Isolation, separation and purification of compound (I) from the reaction mixture can be effected by any suitable separation or purification procedure. In a preferred embodiment, the separation is accomplished by dilution of the reaction mixture with a suitable volume of water, followed by extraction with a suitable aprotic organic solvent, such as ethyl ether, ethyl acetate, methylene chloride, and the like. The organic extract is then washed, dried and concentrated to provide compound (I), which may then be further purified by techniques known to those skilled in the art. In another preferred embodiment, the reaction mixture is diluted with water, and the resulting precipitate is isolated by filtration and washing to provide compound (I), which may then be further purified by conventional techniques.

In this embodiment, the present invention is also directed to a 25 compound represented by formula (VIII):

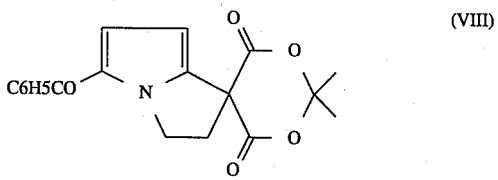

as well as to a method for preparing compound (VIII) which comprises cyclizing, via a free radical ring closure reaction, a compound represented by formula (VII):

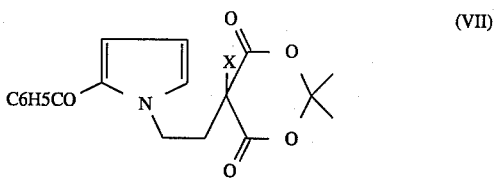

wherein X is defined as set out above. The present invention is further directed to compound (VII) as well as to a method for preparing compound (VII) which comprises treating a compound represented by formula (VI):

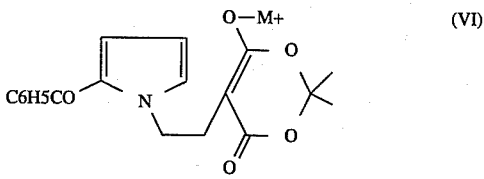

with an electrophilic halogenous reagent, wherein M+ is an alkali metal cation. A preferred electrophilic halogenous reagent is pyridinium bromide perbromide and a preferred alkali metal cation is sodium.

As utilized herein, the term "lower-alkyl" refers to branched and unbranched hydrocarbon groups containing from 1 to 4 carbon atoms, preferably from 1 to 2 carbon atoms, more preferably methyl. The term "halogen", as used herein, refers to the chemically related elements consisting of fluorine, chlorine, bromine and iodine, preferably bromine and iodine.

The present invention is further illustrated by the following examples which are presented for purposes of demonstrating, but not limiting, the preparation of the compounds and compositions of this invention.

EXAMPLES

Route 1

Preparation of 4-(2-Benzoylpyrrol-1-yl)butyric acid methyl ester (III), (Step 1, Scheme 1).

Compounds of the type having Formula II can be prepared according to known procedures (*J. Org. Chem.* 1977, 42, 4248.) and used in Step 1.

A solution of 2-benzoylpyrrole (II, 20.0 g, 117 mmoles) in 50 mL of anhydrous tetrahydrofuran was added dropwise to a nitrogen blanketed stirred suspension of sodium hydride (129 mmoles) in 300 mL of anhydrous tetrahydrofuran over the course of 30 minutes. The reaction mixture was stirred under a nitrogen atmosphere for 1 hour after which gas evolution had ceased. The tetrahydrofuran was then evaporated under reduced pressure to leave the 1-sodio-2-benzoylpyrrole as a yellow solid gamma-Butyrolactone (11.0 g, 128 mmoles) was added to the solid and this mixture was protected from moisture with a calcium sulfate drying tube and heated to 135° C. for 5 hours. After being cooled to room temperature, the resulting solid was dissolved in 1% aqueous sodium hydroxide (500 mL) and extracted with ethyl ether (2×300 mL). The aqueous phase was then acidified to pH 2 by dropwise addition of concentrated hydrochloric acid with vigorous stirring. The acidified aqueous solution was extracted with two portions of ethyl acetate (350 mL, 150 mL) and the combined ethyl acetate extracts were dried over anhydrous sodium sulfate and evaporated under reduced pressure to give 4-(2-benzoylpyrrol-1-yl)butyric acid (III, 27.61 g, 92%). $^1$H NMR (CDCl$_3$): delta 2.18 (m, 2H), 2.40 (t, J=7 Hz), 4.48 (t, J=7 Hz, 2H), 6.17 (m, 1H), 6.75 (m, 1H); 6.99 (m, 1H), 7.41–7.55 (complex m, 3H), 7.77 (m, 2H). This acid was of sufficient purity to proceed with the esterification step without further purification.

4-(2-Benzoylpyrrol-1-yl)butyric acid (8.86 g, 34.4mmoles), prepared as above, was dissolved in methanol (200 mL) and 3 drops of concentrated sulfuric acid were added. The solution was heated at reflux for 1.5 hours followed by addition of 10 mL of 20% aqueous sodium carbonate and evaporation of the methanol under reduced pressure. The residue was dissolved in methylene chloride (250 mL), washed with brine (75 mL), and the methylene chloride phase was dried over anhydrous sodium sulfate and evaporated under reduced pressure to give a quantitative yield of 4-(2-benzoylpyrrol-1-yl)butyric acid methyl ester (III). $^1$H NMR, (CDCl$_3$): delta 2.17 (m, 2H), 2.36 (t, J=7 Hz), 3.37 (s, 3H), 4.47 (t, J=7 Hz, 2H), 6.17 (m, 1H), 6.74 (m, 1H), 6.98 (m, 1H), 7.41–7.55 (complex m, 3H), 7.77 (m, 2H). $^{13}$C NMR (CDCl$_3$): delta 26.66, 30.64, 48.28, 51.54, 108.27, 123.53, 127.91, 129.03, 129.58, 130.80, 131.24, 139.91, 173.24, 185.90.

Preparation of 4-(2-Benzoylpyrrol-1-yl)-2-iodobutyric acid methyl ester (IV), (Step 2, Scheme 1).

Lithium diisopropylamide (5 mmoles) in 2.5 ml heptane/tetrahydrofuran/ethylbenzene was added via a syringe to a solution of 4-(2-benzoylpyrrol-1-yl)butyric acid methyl ester (III, 1.26 g, 4.6 mmoles) in 40 mL of anhydrous tetrahydrofuran cooled to −78° C. under an atmosphere of nitrogen. After being stirred for 45 minutes at −78° C., the reaction mixture was treated with finely crushed iodine crystals (1.24 g, 4.9 mmoles) and then warmed to room temperature. The reaction mixture was then quenched with brine (50 mL) and extracted with ethyl ether (3×50 mL) and the combined ethyl ether fractions dried over anhydrous magnesium sulfate. The ethyl ether extract was evaporated under reduced pressure to give a brown oil which was purified by preparative radial chromatography on silica gel eluting with 20% ethyl acetate in hexane to give 4-(2-benzoylpyrrol-1-yl)-2-iodobutyric acid methyl ester as a yellow oil (IV, 0.68 g, 37%). $^1$H NMR (CDCl$_3$): delta 2.4–2.65 (m, 2H); 3.73 (s, 3H); 4.25–4.4 (m, 2H); 4.62 (m, 1H); 6.18 (dd, 1H); 6.76 (dd, 1H); 7.01 (dd, 1H); 7.4–7.56 (m, 3H); 7.76 (dd, 2H). $^{13}$C NMR (CDCl$_3$): delta 16.3, 37.3, 48.6, 52.9, 108.6, 123.7, 127.9, 129.0, 129.2, 130.8, 131.3, 140.0, 171.7, 186.4.

Alternate Preparation of 4-(2-Benzoylpyrrol-1-yl)-2-iodobutyric acid methyl ester (IV), (Step 2, Scheme 1).

A solution of lithium diisopropylamide (30 mmoles) in 15 mL heptane/tetrahydrofuran/ethylbenzene was added via syringe to a solution of 4-(2-benzoylpyrrol-1-yl)butyric acid methyl ester (III, 6.25 g, 23 mmoles) and trimethylsilyl chloride (13.25 g, 122 mmoles) in 40 mL of anhydrous tetrahydrofuran cooled to −78° C. under an atmosphere of nitrogen. After being stirred at −78° C. for 45 minutes, the reaction mixture was treated with a solution of iodine monochloride (3.75 g, 23 mmole) in 7 mL of dry dichloromethane and the reaction was stirred at −78° C. for an additional 30 minutes followed by warming to room temperature. The reaction was then diluted with 100 mL of diethyl ether and poured into 200 mL of cold (5° C.) 10% $Na_2CO_3$ solution and stirred for 30 minutes. The organic layer was separated, dried over $MgSO_4$ and concentrated to give crude product containing 38% 4-(2-benzoylpyrrol-1-yl)-2-iodobutyric acid methyl ester (IV) as shown by $^1H$ NMR. The crude product can be used as is or further purified by chromatography on silica.

Preparation of 5-Benzoyl-1,2-dihydro-3H-pyrrolo[1,2-a]pyrrole-1-carboxylic acid methyl ester (V), (Step 3, Schemes 1 and 2).

A 1.0N solution of triethylborane in hexane (1.6 mL, 1.6 mmoles) was added to a stirred solution of 4-(2-benzoylpyrrol-1-yl)-2-iodobutyric acid methyl ester (IV, 530 mg, 1.3 mmoles) in dimethylsulfoxide (5 mL) under normal air atmosphere. After 1 hour, additional triethylborane (1.0 mL, 1.0 mmole) in hexane was added and the reaction was stirred. After 30 minutes, the reaction was diluted with brine (50 mL) and extracted with diethyl ether (2×50 mL). The organic layer was dried over $NaSO_4$ and evaporated. The crude product was purified by flash chromatography on silica eluting with 1:4 ethyl acetate/hexane to give pure 5-benzoyl-1,2-dihydro-3H-pyrrolo[1,2-a]pyrrole-1-carboxylic acid methyl ester (V, 220 mg, 61%) as an amber oil. $^1H$ NMR (CDCl$_3$): delta 2.75–3.0 (m, 2H); 3.76 (s, 3H); 4.07 (dd, 1H); 4.38–4.61 (m, 2H); 6.09 (d, 1H); 6.81 (d, 1H); 7.4–7.55 (m, 3H); 7.80 (dd, 2H). $^{13}C$ NMR (CDCl$_3$): delta 30.9, 42.3, 7.4, 52.5, 103.0, 124.8, 127.0,128.0, 128.8, 131.3, 139.1, 142.2, 171.6, 184.8.

Alternative Preparation of 5-Aroyl-1,2-dihydro-3H-pyrrolo[1,2-a]pyrrole-1carboxylic acid methyl ester (V), (Step 3, Schemes 1 and 2).

4-(2-Benzoylpyrrol-1-yl)-2-iodobutyric acid methyl ester (IV, 3.17 grams, 8 mmol) was dissolved in dimethylsulfoxide (32 mL). Iron (II) sulfate heptahydrate (230 mg, 0.827 mmol) was added, and the mixture was stirred for 5 minutes. Hydrogen peroxide (30% aqueous solution, 6 mL) was added dropwise while the internal temperature of the reaction was kept below 35° C. by application of an external water bath. After 45 minutes, TLC (4:1 hexane:ethyl acetate, silica) indicated the reaction was about 60% complete. Additional hydrogen peroxide (2 mL) was added. After 20 minutes more, an additional 2 mL of peroxide and 70 mg of iron sulfate were added) and 15 minutes later, an additional 0.5 mL of peroxide. 20 Minutes after the final peroxide addition, the mixture was poured into water (200 mL). The resulting mixture was extracted with ether (50 mL), then saturated with sodium chloride and extracted twice more with ether. The combined organic extracts were washed twice with water (50 mL each), then once with brine (25 mL), dried over magnesium sulfate, and evaporated in vacuo to afford ketorolac methyl ester (2.095 g, still containing traces of ether (1%) and DMSO (<0.3%) by NMR. Yield calculated on the basis of weight and NMR purity is 96%.

The product may be crystallized from methanol, m.p. 80°–82° C.

Preparation of the Sodium Salt of 1-[2-(4,6-Dioxo-2,2-dimethyl-1,3-dioxan-5-yl)ethyl]-2-(benzoyl)pyrrole (VI), (Step 1, Scheme 2).

2-Benzoylpyrrole (II, prepared according to known procedures, e.g., *J. Org. Chem.* 1977, 42, 4248) is N-alkylated with spiro[2,5]-5,7-dioxa-6,6-dimethyloctane-4,8-dione to form the cyclic diester, 1-[2-(4,6-dioxo-2,2-dimethyl-1,3-dioxan-5-yl)ethyl]-2-(benzoyl)pyrrole (VI), according to known procedures, e.g., U.S. Pat. No. 4,347, 187.

Preparation of 4-(2-Benzoylpyrrol-1-yl)-2-iodobutyric acid ester (IV), (Step 2a, Scheme 2).

The sodium salt of 1-[2-(4,6-dioxo-2,2-dimethyl-1,3-dioxan-5-yl)ethyl]-2-benzoylpyrrole (VI, 3.63 grams, 10 mmol) was suspended in tetrahydrofuran (20 mL), and the mixture was cooled in a dry ice/acetone bath. A solution of iodine monochloride (1.62 grams, 10 mmol) in methylene chloride (10 mL) was added dropwise over 15 minutes. The mixture was stirred at −78° C. for 15 minutes longer, then allowed to warm slowly to room temperature. A solution of sodium methoxide (from 320 mg of sodium metal in 10 mL of methanol) was added, and the mixture was stirred at room temperature for 60 minutes. The mixture was heated to reflux for 5 minutes, then allowed to cool to room temperature.

The mixture was poured over ice (100 grams) and extracted three times with 25 mL portions of ether. The combined ether extracts were washed with 5% aqueous sodium bicarbonate, dried over magnesium sulfate, and concentrated in vacuo to afford the iodoester, 4-(2-benzoylpyrrol-1-yl)-2-iodobutyric acid methyl ester, (IV, 3.22 grams, 81%). This material was essentially pure by NMR, and was used directly in the ring-closure step.

Alternative Preparation 4-(2-Benzoylpyrrol-1-yl)-2-iodobutyric acid methyl ester (IV) Using Methyl Hypoiodite, (Step 2b, Scheme 2)

Sodium methoxide solution was prepared by dissolving metallic sodium (1.38 g, 60 mmol) in methanol (30 mL). This solution was diluted with anhydrous tetrahydrofuran (100 mL) and cooled to −30° C. A solution of iodine monochloride (8.97 g, 55.3 mmol) in dichloromethane (30 mL) was added dropwise to the stirred alkoxide solution. The resulting solution was stirred for 2 minutes, then the sodium salt of 1-[2-(4,6-dioxo-2,2-dimethyl-1,3-dioxan-5-yl)ethyl]-2-benzoylpyrrole (VI, 18.15 g, 50 mmol) was added as a solid. The mixture was stirred for 90 minutes at −30° C., then allowed to warm to 22° C. and stirred for an additional 18 hours. The reaction mixture was poured into 150 mL of 2% aqueous sodium sulfite solution in a separatory funnel, and the reaction flask was washed with 10 mL of diethyl ether, which was added to the separatory funnel. The mixture was shaken thoroughly, and the phases were separated. The aqueous phase was extracted with diethyl ether (2×20 mL), and the combined organic phase was washed with brine, dried over magnesium sulfate, and evaporated to afford 4-(2-benzoylpyrrol-1-yl)-2-iodobutyric acid methyl ester (IV, 18.16 g, 91.5%), identical to the material prepared by the method described above.

Route 2

Preparation of 1-[2-(5-Bromo-4,6-dioxo-2,2-dimethyl-1,3-dioxan-5-yl)ethyl]-2-(benzoyl)pyrrole (VIIA), (Step 2, Scheme 3).

Pyridinium bromide perbromide (11.51 g, 36 mmoles) in tetrahydrofuran (25 ml) was added dropwise at 0°–5° C. to a vigorously stirred suspension of the sodium salt of 1-[2-(4,6-dioxo-2,2-dimethyl-1,3-dioxan-5-yl)ethyl]-2-benzoylpyrrole (VI, prepared as described above, 13.5 g, 37.2 mole). The mixture was stirred for 1 hour at 0°–5° C. The mixture was then poured into water (600 ml) and extracted three times with diethyl ether (100 ml, then 2×50 ml). The organic phase was separated and washed with two 200 ml portions of water, dried over magnesium sulfate and evaporated to afford crystalline 1-[2-(5-bromo-4,6-dioxo-2,2-dimethyl-1,3-dioxan-5-yl)ethyl]-2-(benzoyl)pyrrole (VIIa). The product could be recrystallized from ethyl acetate/hexane to give material with the following properties: m.p. 89°–91° C. $^1$H NMR (CDCl$_3$): delta 1.81 (s, 3H); 2.00 (s, 3H); 3.19 (t, 2H); 4.58 (t, 2H); 6.19 (dd, 1H); 6.71 (dd, 1H); 6.89 (dd, 1H); 7.4–7.55 (m, 3H); 7.78 (dd, 2H). $^{13}$C NMR (CDCl$_3$): delta 26.8, 28.9, 39.7, 43.5, 45.8, 107.3, 123.5, 127.9, 129.2, 130.3, 131.4, 139.1, 163.0, 186.9.

Preparation of 5-Benzoyl-1,2-dihydro-3H-pyrrolo[1,2-a]pyrrole-1-spiro-5'-(2',2'-dimethyl-4',6'-dioxo)-1',3'-dioxolane (VIII), (Step 3, Scheme 3).

1-[2-(5-Bromo-4,6-dioxo-2,2-dimethyl-1,3-dioxan-5-yl)ethyl]-2(benzoyl)pyrrole (VII, 4.32 g, 10.3 mmole) and iron (II) sulfate heptahydrate (350 mg, 1.26 mmole) were dissolved in dimethylsulfoxide at 55° C. The reaction flask was immersed in a water bath (23° C.), and hydrogen peroxide (30% aqueous solution, 10 ml) was added dropwise at a rate which maintained an internal temperature of 55°–70° C. When addition was complete, the mixture was stirred for 25 minutes at 55° C., during which time crystallization of the product was observed. The resulting semisolid mass was washed out of the flask into rapidly stirred 5% aqueous sodium bicarbonate solution (350 ml) with ethyl acetate (100 ml), and the resulting two-phase mixture was stirred vigorously for 30 minutes. The phases were separated, and the aqueous phase was extracted twice with 50 ml portions of ethyl acetate. The combined organic phases were dried over magnesium sulfate and evaporated to afford 5-benzoyl-1,2-dihydro-3H-pyrrolo[1,2-a]pyrrole-1-spiro-5'-(2',2'-dimethyl-4',6'-dioxo)-1',3'-dioxolane (VIII) as a sticky solid still containing some dimethylsulfoxide. Recrystallization of the product from aqueous acetone afforded pure product, which displayed the following properties: m.p. 171°–172° C. $^1$H NMR (CDCl$_3$): delta 1.85 (s, 3H); 1.93 (s, 3H); 3.26 (t, 2H); 4.78 (t, 2H); 6.03 (d, 1H); 6.83 (d, 1H); 7.44–7.58 (m, 3H); 7.83 (dd, 2H). $^{13}$C NMR (CDCl$_3$): delta 28.8, 29.0, 41.5, 47.5, 52.4, 102.0, 106.6, 124.3, 128.1, 128.8, 128.9, 129.0, 131.7, 138.1, 167.3, 175.2.

Hydrolysis and Decarboxylation of 5-Benzoyl-1,2-dihydro-3H-pyrrolo[1,2-a]pyrrole-1-spiro-5'-(2',2'-dimethyl-4',6'-dioxo)-1',3'-dioxolane (VIH) to 5-Benzoyl-1,2-dihydro-3H-pyrrolo[1,2-a]pyrrole-1-carboxylic acid (I), (Step 4, Scheme 3).

5-Benzoyl-1,2-dihydro-3H-pyrrolo[1,2-a]pyrrole-1-spiro-5'-(2',2'-dimethyl-4',6'-dioxo)-1',3'-dioxolane (VIII) (63 mg, 0.19 mmol) was dissolved in a mixture of trifluoroacetic acid (1.5 mL) and water (0.5 mL), and the mixture was heated at reflux for 30 minutes. The mixture was poured into a mixture of diethyl ether (10 mL) and water (20 mL), shaken, and the phases were separated. The aqueous layer was extracted with diethyl ether (2×5 mL), then the combined organic extracts were washed with water (4×30 mL), dried over magnesium sulfate, and evaporated to afford 5-benzoyl-1,2-dihydro-3H-pyrrolo[1,2-a]pyrrole-1-carboxylic acid (I) (47 mg, quantitative yield), identical with an authentic standard.

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A method for preparing a compound represented by formula (I):

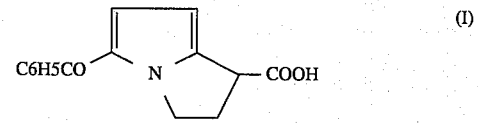

which comprises the sequential steps of cyclizing, via a free radical ring closure reaction, and hydrolyzing a compound represented by formula (IV):

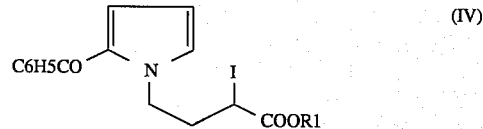

wherein R$_1$ is lower alkyl and recovering said compound of formula (I).

2. The method according to claim 1, wherein R$_1$ is methyl.

3. A compound represented by formula (IV):

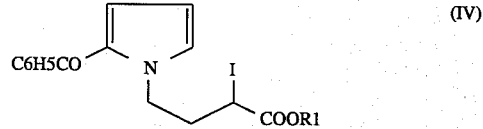

wherein R$_1$ is lower alkyl.

4. The compound according to claim 3, wherein R$_1$ is methyl.

5. A method according to claim 1, wherein said compound represented by formula (IV):

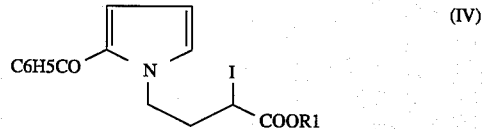

is prepared by the sequential steps of treating a compound represented by formula (III):

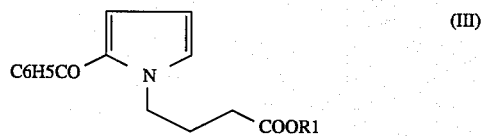

with a strong, non-nucleophilic base and an electrophilic iodogenous reagent, wherein R$_1$ is lower alkyl.

6. The method according to claim 5, wherein R$_1$ is methyl.

7. The method according to claim 5, further comprising the step of treating compound (III) with trialkylsilyl chloride prior to the treatment with the strong, non-nucleophilic base.

8. A method for according to claim 1, wherein said compound represented by formula (IV):

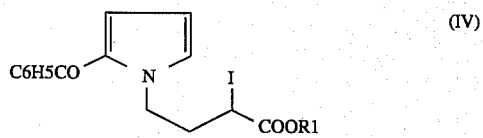

is prepared by the sequential steps of hydrolyzing and decarboxylating a compound represented by formula (VIIb):

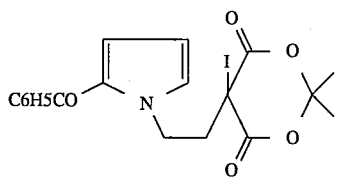

wherein $R_1$ is lower alkyl.

9. The method according to claim 8, wherein $R_1$ is methyl.

10. The method according to claim 8, wherein the compound represented by formula (VIIb):

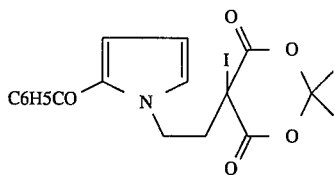

is prepared by the alpha-iodonation of a compound represented by formula (VI):

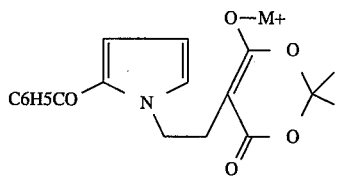

with an electrophilic iodonous reagent, wherein M+ is an alkali metal cation.

11. The method according to claim 10, wherein the electrophilic iodonous reagent is selected from the group consisting of iodine monochloride, N-iodosuccinimide, lower alkyl hypoiodites, and iodine/morpholine complex.

12. The method according to claim 11, wherein the electrophilic iodonous reagent is a lower alkyl hypoiodite.

13. The method according to claim 10, wherein the alkali metal cation is sodium.

14. A method for preparing a compound represented by formula (I):

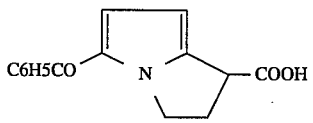

which comprises the sequential steps of hydrolyzing and decarboxylating a compound represented by formula (VIII):

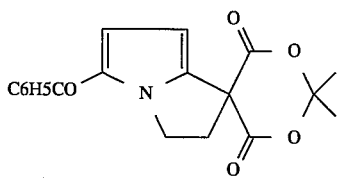

and recovering said compound of formula (I).

15. A compound represented by formula (VIII):

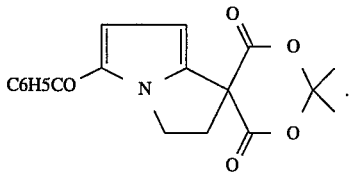

16. A method according to claim 14, wherein said compound represented by formula (VIII):

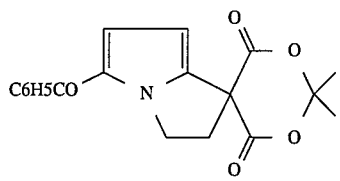

is prepared by cyclizing, via a free radical ring closure reaction, a compound represented by formula (VII):

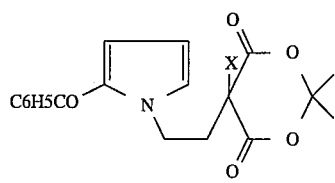

wherein X is bromine or iodine.

17. The method according to claim 16, wherein X is bromine.

18. A compound represented by formula (VII):

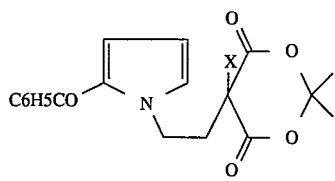

wherein X is bromine or iodine.

19. The compound according to claim 18, wherein X is bromine.

20. A method according to claim 16, wherein said compound represented by formula (VII):

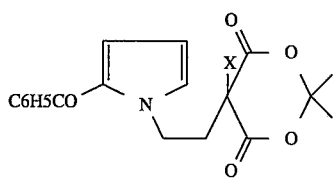

wherein X is bromine or iodine, is prepared by treating a compound represented by formula (VI):

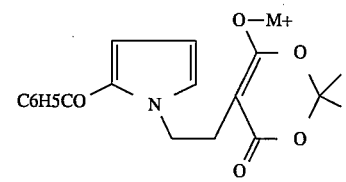

with an electrophilic halogenous reagent, wherein M+ is an alkali metal cation.

21. The method according to claim 20, wherein the electrophilic halogenous reagent is pyridinium bromide perbromide.

22. The method according to claim 20, wherein the alkali metal cation is sodium.

* * * * *